United States Patent
Recker et al.

(10) Patent No.: US 12,139,700 B2
(45) Date of Patent: Nov. 12, 2024

(54) BIOPROCESS CONTROL DEVICE AND BIOPROCESS SYSTEM

(71) Applicant: Eppendorf AG, Hamburg (DE)

(72) Inventors: Wolfgang Recker, Aachen (DE); Guido Ertel, Dormagen (DE); Falk Schneider, Aachen (DE); Tristan Hufen, Kelmis (BE)

(73) Assignee: EPPENDORF SE, Hamburg (DE)

( * ) Notice: Subject to any disclaimer, the term of this patent is extended or adjusted under 35 U.S.C. 154(b) by 0 days.

(21) Appl. No.: 16/955,816

(22) PCT Filed: Dec. 10, 2018

(86) PCT No.: PCT/EP2018/084113
§ 371 (c)(1),
(2) Date: Jun. 19, 2020

(87) PCT Pub. No.: WO2019/121089
PCT Pub. Date: Jun. 27, 2019

(65) Prior Publication Data
US 2021/0095239 A1 Apr. 1, 2021

(30) Foreign Application Priority Data
Dec. 19, 2017 (EP) .................................... 17208569

(51) Int. Cl.
*C12M 1/36* (2006.01)
*C12M 3/00* (2006.01)

(52) U.S. Cl.
CPC ............ *C12M 41/48* (2013.01); *C12M 23/44* (2013.01)

(58) Field of Classification Search
CPC .............................. C12M 41/48; C12M 23/44
See application file for complete search history.

(56) References Cited

U.S. PATENT DOCUMENTS

| 4,424,559 A | * | 1/1984 | Lorincz ................. G05D 27/02 422/62 |
| 6,642,018 B1 | | 11/2003 | Eisfeld et al. |

(Continued)

FOREIGN PATENT DOCUMENTS

| DE | 102005036763 A1 | 2/2007 |
| DE | 102008049722 A1 | 4/2010 |

(Continued)

OTHER PUBLICATIONS

International search report for patent application No. PCT/EP2018/084113 dated Apr. 29, 2019.

*Primary Examiner* — Liban M Hassan
(74) *Attorney, Agent, or Firm* — Bachman & LaPointe, P.C.

(57) ABSTRACT

The invention relates to a A bioprocess control device having a number of control function units (12, 30) which are accommodated in a device housing (10), are designed for bioprocesses and are configured for carrying out control, conveying, measuring and/or sensor functionalities and In order to accommodate the plurality of control function units, the device housing has modular drawer assemblies (14, 32) which, relative to stationary housing frame of the device housing in an opening position and/or removal position, allow access for configuration and/or assembly to the control function unit accommodated in a relevant drawer assembly, and, in an operating and closure position which can be locked by locking means (60, 58), produce an electrically supplying as well as electronically function-identifying contact between the control function unit and the housing frame and/or electrical power supply (40) as well as system identification means (42) associated with a further drawer assembly.

11 Claims, 3 Drawing Sheets

(56) References Cited

U.S. PATENT DOCUMENTS

| | | | |
|---|---|---|---|
| 2005/0051723 A1* | 3/2005 | Neagle | G01N 21/253 |
| | | | 250/306 |
| 2010/0305759 A1 | 12/2010 | Lemaire et al. | |
| 2017/0022468 A1 | 1/2017 | Cesarini et al. | |

FOREIGN PATENT DOCUMENTS

| | | |
|---|---|---|
| DE | 102012102918 A1 | 10/2013 |
| EP | 3188576 A1 | 7/2017 |
| JP | S62-171674 A | 7/1987 |
| JP | 2009502183 A | 1/2009 |
| JP | 2011509685 A | 3/2011 |
| WO | 2004051267 A2 | 6/2004 |
| WO | 2010025302 A2 | 3/2010 |
| WO | 2017032847 A1 | 3/2017 |
| WO | 2017109083 A1 | 6/2017 |

\* cited by examiner

BIOPROCESS CONTROL DEVICE AND BIOPROCESS SYSTEM

BACKGROUND OF THE INVENTION

The present invention relates to a bioprocess control device according to the preamble of the main claim. Furthermore, the invention relates to a bioprocess system having such a control device, and the invention relates to a method for configuring and/or modifying such a system.

Such a device is known from the state of the art in the context of the operation of bioprocess apparatuses and is used for the specific control and monitoring of biological trial and development processes which take place in suitable bioreactors, for example.

For example, the applicant offers a series of generic bioprocess control devices under the trademark BioFlo which allow a user to monitor and to control the processes, which are set up or to be set up, in a user-friendly, reliable and up-to-date manner, the bioprocess control devices being configured for predefined biological processes. The generic term of the present invention typically including a plurality of control function units received in a device housing relates to a plurality of bioprocesses to be controlled or to be monitored in a generic manner; the range of application of the generic devices, which are usually used in development processes and other process technologies which are upstream of a large-volume production, ranges from the development and production (typically limited to small experimental quantities) of media such as vaccines, a process development with respect to cell cultures or other microbiological applications to the cloning and screening of cell lines and the cultivation of stem cells. Accordingly, there are different variants of such systems which are offered as generic systems and which are typically standardized or preconfigured for an intended use, and the type and number of the control function units to be used for the different processes is broad—corresponding to the requirements of the respective bioprocess or the process development, said control function units are configured as control, conveying, measuring and/or sensor units and are normally assigned to a bioprocess reactor in a suitable manner by means of conventional lines, hoses, cables or the like; this can normally be realized in the immediate vicinity, for example on a common table or support unit.

However, the present laboratory and research or development context of the use of the bioprocess control devices according to the preamble leads to the fact that long-lasting bioprocess are rarely operated or controlled, regular re-configurations or an exchange of the known bioprocess control device (in connection with a corresponding adjustment of the bioreactor equipment) thus being required when a development or testing program is changed, said re-configuration or the exchange being normally required within a range from one to a few weeks to a few months.

Referring to the known and generic technology, a configuration and equipping of the control device which is adapted to a following bioprocess for development or testing purposes can be realized by trained personnel of the system manufacturer; alternatively, a testing laboratory environment has a plurality of control devices which are preconfigured in an alternative manner and which can be connected and operated in a suitable manner.

The disadvantage of the technologies which are known from the state of the art is obvious: In particular in the light of increasingly short (development) process cycles and a quicker succession of required exchange or modification measures, an associated frequent modification activity of trained personnel of the manufacturer and the storage of a plurality of preconfigured units (in the respective device housings) are potentially uneconomical—the preconfigured units which are largely unused are to be stored (in the scarce laboratory space) until a configured control device which is provided in a suitable manner is required.

Furthermore, WO 2017/109083 A1 discloses an instrument suitable for processing cells, for example culturing, concentrating or washing said cells, the instrument comprising a housing for accommodating mechanical elements including at least one fluid pump; and a disposable processing kit complementary to the mechanical elements within the housing and comprising a fluid circuit including a fluid reservoir and plural fluid paths capable of carrying fluid flow caused by said pump(s), the instrument further including a mechanism for determining the quantity, or change in quantity of the fluid in the reservoir resulting from said fluid flow, the instrument further comprising a controller operable to control at least the pump.

DE 10 2005 036 763 A1 discloses a system comprising a plurality of incubators, each encompassing a housing, a sample chamber disposed inside the housing for receiving a sample container, a temperature-regulating unit and an electronic controller that controls the temperature-regulating unit. The sample chambers of the incubators can be heated and/or cooled by the temperature-regulating units and the housings of the incubators each have a closable access opening for loading and unloading the sample chamber, the housings of the incubators permitting vertical stacking of the incubators. The incubators each have a bus system cooperating with their electronic controllers, the bus systems of the incubators being connected to one another via connecting elements. The system further comprises a central control unit connected to the bus system of one of the incubators, the electronic controllers of all incubators of the system can therefore be activated individually by the central control unit by virtue of the architecture of the bus system.

WO 2017/032847 A1 discloses a bio manufacturing apparatus comprising a housing, a substantially enclosed bioreactor chamber inside the housing and a further substantially enclosed region inside the housing containing electrical parts and/or electronic control components, the chamber including: a tray for supporting a bioreactor, a tray support including a mechanism rocking the tray in use, the tray including a heater for contacting a bioreactor and heating the same, and the apparatus further comprising secondary heating for heating air surrounding the tray.

WO 2010/025302 A2 describes systems, devices, apparatuses and methods for automated bioprocessing. Examples of suitable protocols and bioprocessing procedures include but are not limited to: immunoprecipitation, chromatin immunoprecipitation, recombinant protein isolation, nucleic acid separation and isolation, protein labeling, separation and isolation, cell separation and isolation, food safety analysis and automated bead based separation.

Said challenges are to be considered in the light of sensitive laboratory environments which are to be protected against contaminations and other environmental influences which are potentially harmful for the bioprocesses; additionally, the sensitive laboratory environments require the accurate and transparent recording and examination of the implemented measures—not least for reasons of quality assurance and product approval.

SUMMARY OF THE INVENTION

Therefore, the object of the present invention is to improve a bioprocess control device with respect to its suitability for a plurality of different bioprocesses, in particular to realize an adjustment or modification or configuration of the control device for consecutive, different bioprocess applications in a simpler, more comfortable and more economical manner without any risk of misuse, other process burdens or negative impacts by external influences. Furthermore, the requirements for a reliable and verifiable configuration and a subsequent (testing) operation of such control devices for bioprocesses are to be created, said technology being particularly characterized by a short time of process, process development and adjustment—compared to a large-scale production of biological and biotechnological products.

Said object is attained by the bioprocess control device having the features disclosed herein; advantageous embodiments of the invention are also disclosed herein and in the dependent claims. Within the scope of the invention, protection is also sought for a bioprocess control system which has the bioprocess control device according to the invention and a plurality of control function units which are provided within the scope of said control device, a suitability for at least two bioprocess to be controlled in an alternative manner in a device housing being enabled within the scope of said system by selecting and exchanging the required control function units in a corresponding manner. The invention is particularly suitable for a laboratory, research and process development context in which such re-configurations occur more frequently, compared to stationary production processes, and the advantages according to the invention to be described below are therefore obvious.

In an advantageous manner according to the invention, the device housing of the bioprocess control device has modular drawer assemblies which are realized and provided in order to receive the control function units. Said drawer assemblies are realized in interaction with stationary housing frame means of the device housing in such a manner that the drawer assemblies allow access for configuration and/or assembly to the control function unit received in the corresponding drawer assembly, the drawer assembles being in an opening and/or removal position which is preferably separated or separable from the housing frame means (and allows for a removal from the housing frame, for example). In said state, the invention provides to assign a desired or required control function unit to a drawer assembly—preferably realized in an identical or standardized manner within the scope of the invention—normally by means of screwing or similar detachable fixation measures to or in the drawer assembly.

According to the invention, the drawer assemblies are also realized in interaction with the device housing or the frame means in such a manner that the respective drawer assembly can be displaced into an operating or closure position, typically by means of insertion or similar actuation measures, in which the drawer assembly can be fixed in a locking manner by means of lock means according to the invention. According to the invention, an electrically supplying and electrically function-identifying contact between the control function unit (received in the drawer assembly) and electrical energy supply means (on the one hand) and system identification means (on the other hand) are realized in said position, wherein the system identification means can be assigned to and provided or assembled at the frame means in a stationary manner, or, additionally or alternatively, an additional drawer assembly. According to an embodiment of the invention, said units are configured in such a manner that an exchange of the drawer assemblies can even be realized during the bioprocess control operation of the device and the flexibility is further optimized.

Said manner according to the invention allows for a modification of generic control devices in a highly flexible manner and, in particular, by untrained configuration personnel without any risk of misconfigurations or a malfunction: By means of the measure according to the invention to identify a drawer assembly (which allows for a simple exchange) inserted into the device housing with respect to its respective function (i.e. the inherent functionality and the intended function of the respective control function unit), it is possible to detect said control function unit in a suitable manner by means of the system technology (and in particular by the system identification means according to the invention), to integrate said control function unit into an overall system functionality of the bioprocess control device and to perform a suitable control without any additional knowledge or adjustment measures by the operating personnel realizing the modification being required—even unsuitable or error-prone or defective control function units can be detected by a corresponding identification and reaction by means of the system identification means and can be taken into account before additional operation or process problems arise, for example by a corresponding signal output or a deactivation of said units.

Additionally, the lock means according to the invention (more preferably acting in a mechanical manner) ensure an operation of the control function units received in the respective drawer assemblies which is mechanically safe (and secured against an unintended pulling out or falling out) and said lock means, which are preferably realized as mechanical rod and/or bracket units, allow for a mechanical identification of a drawer assembly and control function unit which are incorrectly placed at or in the operating and closure position and said lock means therefore allow for a prevention of potential connection or contact problems.

As a result, the present invention allows for the addressing of adjustment problems in a surprisingly simple manner with respect to changing testing and development environments which arise in the present bioprocess context, the present technology created by the invention significantly increasing the flexibility and the adjustability of the system provided or to be provided in the device housing and composed of control function units which have different purposes and functionalities.

According to an embodiment, control function units to be assembled at or in drawer assemblies are provided within the scope of the invention, said control function units having a plurality of different applications and functionalities—besides (in particular modular) fluid transport means, such as pump devices of any kind for liquids or gases, in particular pump control devices can be provided in drawer assemblies according to the invention, said pump control devices communicating with pumps or similar fluid transport means provided at or in the reactor vessel in a manner known per se. This applies equally to valve devices (or combinations of valves and pumps, for fluid heating and/or fluid cooling devices), any fluid handling task thus being settable, configurable and operable within the scope of the present invention corresponding to the proven technology and the flexibility is significantly increased. Similarly, control function units according to the invention can realize functionalities of gas sensor devices, liquid sensor devices, electrical and/or optical measuring devices, and can be used as control devices for bioreactor stirring means or similar mechanical movement actuators and can realize functionalities of the electrical energy input in bioreactors or similar vessels. It is evident that a wide range of functionalities to be used in a suitable manner can be realized, in particular by the configurability and adjustability to different laboratory or process procedures which is simplified by means of the present invention.

In order to optimize the realization of the function identification according to the invention between the drawer assembly and the device housing (or stationary housing frame means), the drawer assemblies have function identification and parameter means which are preferably realized as electronic devices and which are realized on an electrical circuit board which is provided at or in the drawer assembly, for example by means of a microcontroller. Said function identification and parameter means provide the identification data which identify the assembled control function unit and electrical parameter data which are assigned to the control function units to be processed by the system identification means (typically on the side of the housing) via an electronic interface of the drawer assembly—for example via an electrical contact strip, a bus connection or the like. In a particularly advantageous and additional embodiment, the specific realization of the drawer assembly allows for an identification of a function type, a serial and/or version number, a required operating voltage or other data relating to an operation of the drawer assembly or its control function unit (said identification being normally realized in an automatic and program-supported manner, for example if it is realized by means of a microcontroller unit). In particular, said identification and communication processes can take place during or after completion of the mechanical assembly operations and can also perform an examination, for example in the abovementioned manner, with respect to an incorrect equipping, with respect to processes which are out of date and/or which are no longer useful for a desired process or with respect to similar errors. In particular such problematic configuration states and a proper (and technically up-to-date) configuration which is suitable for a laboratory operation can be signaled via signal, communication and/or alarm means to be provided according to the embodiment.

In particular the potential problem of a (parameter, operating system or program) actualization of respective control function units (assembled in drawer assemblies) can be addressed in an additional embodiment according to the invention by means of communication and/or actualization means which are assigned to the function identification or parameter means according to the invention in the embodiment in such a manner that, in response to an electronic recording of the identification or parameter data, a modification of said data (in particular in the form of actualization data) can be realized. In this regard, it is useful to store the data on the side of the drawer, more preferably in the form of non-volatile storage units, such an actualization process thus not being required for subsequent, later configurations and uses.

With respect to the documentation, verifiability and traceability of the methods and method steps, including possible configuration and re-configuration steps, which are important for biological and biotechnological processes, especially in a laboratory, research and development environment, additional advantageous embodiments provide to assign electronic process protocol means to the function identification and parameter means (i.e. for a respective drawer assembly), additionally or alternatively to the system identification means (of the device housing or of the stationary housing frame means) in such a manner that said process protocol means record, store and—for a processing outside the system—provide operating or configuration data which correspond to an operation and/or a configuration; this is normally realized for long periods of time. In an advantageous manner according to the embodiment, such a protocol-like recording is realized in an overarching manner for a respective overall configuration in a device housing; additionally or alternatively, said recording can be realized individually for each drawer assembly, not least because a convenient electronic infrastructure in the form of a microcontroller assembly is provided in an advantageous manner, individual operating histories of respective (assembled) drawer assemblies thus being recordable and traceable, even for several device housings.

Mechanically, the housing frame means according to the invention of the device housing offer a plurality of shaft-like receptions for the drawer assemblies in such a manner that a respective drawer assembly can be placed at several alternative positions in respective shaft-like receptions, in particular without the need for specific reception or assembly locations in the form of defined receptions. This results in a high degree of flexibility in the configuration or in the flexible exchange of the drawer assemblies (carrying the control function units) in relation to the stationary frame means (within the scope of the present invention, "stationary" is to be understood in such a manner that, in contrast to the insertable and extractable and potentially removable drawer assemblies, a mechanical frame and reception structure of the housing frame means, in particular in the form of shaft-like receptions provided according to the embodiment, remains stationary).

In an additional advantageous embodiment, the drawer assemblies are realized in such a manner with respect to respective front outer surfaces that a common, (at least sectionwise) continuous and preferably plane outer surface of the device housing is realized in the operating or locking position according to the invention. It is thus visually recognizable that the plurality of inserted drawer assemblies is in a proper assembly and locking position (and does not protrude, for example), and the continuous outer surface which is enabled by said realization is particularly preferably suitable for the treatment with detergents and disinfectants, said treatment being required in a biological or biotechnical laboratory context in order to apply the hygiene and cleanliness conditions. To this end, an additional embodiment of the invention provides to realize the front outer surfaces of the drawer assemblies in particular in a tile-like or mosaicked manner and to dispose said front outer surfaces so as to be adjacent to one another in such a manner that the desired consistency of the total surface is realized and the gap widths in the transition are as small as possible. In order to realize a complementary or additional support, the remaining gaps can be filled with sealing means or similar accessories, in particular liquid detergents thus not being able to penetrate into the device housing and to damage the functionality.

In a particularly advantageous manner with respect to the mechanism and the functionality, an embodiment provides to realize the lock means according to the invention in such a manner that the lock means which are realized as a lock assembly engage in a mechanical manner on an abutment and/or locking section of a drawer assembly and can in particular be pushed onto said abutment and/or locking section. Accordingly, a blocking friction-type connection is realized between the drawer assembly and the stationary housing frame means, an unintended pulling out and corresponding contact and connection problems thus being reliably avoided.

In an additional advantageous embodiment, such a lock assembly is realized in a rod- or bracket-like manner and is guided in a lateral and abeam manner (i.e. at an angle of approx. 90° to the insertion or extraction direction of the drawer assemblies in relation to the housing frame means). In this way, a plurality of drawer assemblies (typically disposed above one another in shaft-like receptions) can be simultaneously realized by one locking process, for example by means of a lock assembly which is realized in a corresponding manner and which has several arms; additionally, an incomplete alignment of the abutment or locking section with a frame section which is configured for the friction-type connection indicates an incorrect insertion state of a drawer assembly and the locking is therefore hampered.

Within the scope of the invention, the contact, in particular between control function units and housing frame means or contact members to be provided for the interfaces which are assigned to the drawer assemblies, is preferably realized in a sprung manner in order to realize a tolerance compensation which improves the contact quality and in order to realize minimized transition resistances of respective electrical contacts, the minimized transition resistances also minimizing possible errors.

As a result, the present invention allows for the realization of flexible bioprocess control devices which can be modified in a simple and quick manner and which can be used for a wide range of applications, the possibilities of a flexible use and a new configuration or re-configuration being significantly improved compared to the generic state of the art (thereby also minimizing errors, including misconfigurations, a defective setup or defective selection of control function units).

Within the scope of the system concept which is also claimed according to the invention, control function units are preferably provided for more than one bioprocess and, according to an embodiment, it is also possible to complement the device housing according to the invention with housing frame means to be additionally provided outside the housing, so that it offers additional flexible extension options in the case of particularly complex control function units and a number of control function units which is higher than the number of drawer positions (shaft-like receptions) of the principal device housing. In an additional and advantageous embodiment, such an additional device housing (which, according to the invention, also embodies the bioprocess control device according to the main claim) can be realized as a passive housing unit, namely in particular in that the additional drawer assemblies (including the corresponding additional control function units) received or to be received in the additional housing frame means outside the housing use the electrical supply means (i.e. a central power supply) and the (central) system identification means of the device housing by means of a suitable (e.g. wired) coupling with the device housing.

Within the scope of the invention, protection is also sought for a method for configuring and/or modifying a bioprocess system which is in particular realized by at least one bioreactor in interaction with the bioprocess control device according to the invention and with the control function units received in the drawer assemblies. Said method particularly provides the exchange, the complementing or the re-configuration of at least one of the control function units (or of the corresponding drawer assembly) for a change from a first biological, pharmaceutical, chemical and/or biotechnical process to a second process of this sort, the present invention thus being particularly characterized by the significant time reduction and flexibility within the scope of a configuration and modification process. In response to the assembly of a plurality of drawer assemblies in the device housing, additionally or alternatively in response to the replacement of the at least one drawer assembly, an additional embodiment of said method provides the realization of an automatic identification, complementation or, alternatively, an automatic parameterization of the control function units assembled together with the drawer assemblies with respect to a central control or identification unit (on the side of the housing).

BRIEF DESCRIPTION OF THE DRAWINGS

Further advantages, features and details of the invention can be derived from the following description of preferred exemplary embodiments and from the drawings.

In the following.

DETAILED DESCRIPTION

Figure 1:
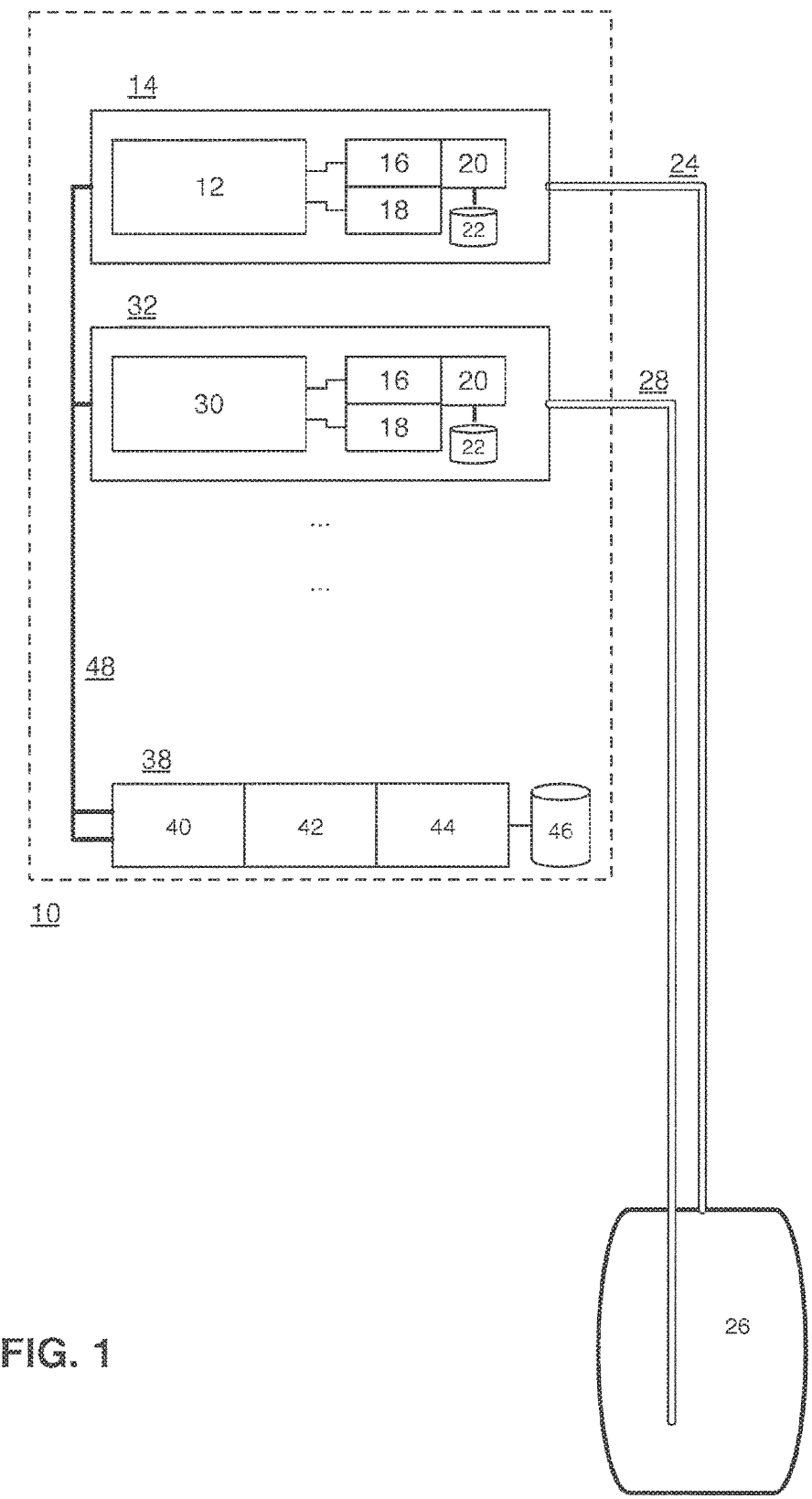
FIG. 1 is a schematic block diagram of the bioprocess control device according to the invention having essential functional components according to a first exemplary embodiment.

FIG. 1 shows the logical functional structure as a functional diagram of the bioprocess control device according to a first exemplary embodiment of the present invention. Dotted frame line 10 illustrates a device housing and a frame structure (housing frame means) realized therein and in which shafts for the detachable or removable reception of control function units 12, 30 received in drawer assemblies 14, 32 are initially realized. Additionally, panel-like housing walls or similar additional housing components are provided (in a removable manner) at the housing frame means as well as a central system electronics assembly 38 which communicates in an electronic manner (to be described below) with control function units 12, 30 and supplies control function units 12, 30 with operating voltage.

With respect to the mechanism, each of drawer assemblies 14, 32 is realized so as to be identical and exchangeable in such a manner that drawer assemblies 14, 32 can be used at any operational or shaft position inside the housing (cf. the description below in connection with FIGS. 2 to 5). To this end, an interface plug unit (56, FIG. 3) (for example in the form of a power strip) is assigned to each of the drawer assemblies which engage into corresponding plug receptions assigned to a respective shaft position of housing 10 and which can therefore be coupled to supply unit 38 via a central supply and (data) bus line. In a manner known per se, a standardized, digital bus system can be used and a communication by means of determined lines assigned to suitable functional units can be established in order to realize connection 48; additionally, connection 48 provides a (normally uniform) operating voltage for each of the drawer assemblies, the operating voltage being supplied by operating voltage means 40 of central supply unit 38 (which is connected to a line voltage connection in a manner which is not shown).

Each of the control function units assigned to a drawer assembly and assembled on a support unit of the drawer assembly, for example, is realized in order to have or to fulfill a function within the scope of the bioprocess to be displayed or to be supported in reactor 26. For example, control function unit 30 is connected to an interior of reactor 26 via a fluid line 28 which is configured in a suitable manner and, also in an exemplarily manner, control function unit 12 is realized as a gas and temperature sensor which measures a process gas concentration and temperature in the lid area of reactor 26 in the exemplary embodiment of FIG. 1 which is shown in a schematic manner.

Within the scope of the illustrated exemplary embodiment of the present invention, a function identification unit 16 is assigned to each of the control function units, function identification unit 16, as a component of an electronics assembly assigned to the drawer assembly (and typically realized by means of an electronic circuit board which is assembled in each drawer assembly and which includes a microcontroller which is programed in a suitable manner and a peripheral electronics assembly) identifying the type and the specific realization of the connected control function unit, typically after its assembly and when it is inserted into the device housing, and function identification unit 16 supplying said information for further examination and processing to central system identification means 42 via connection system 48. In this way, in particular a central sequence control (not shown in detail) can first detect the presence of the control function unit (which is desired or required for the present bioprocess) and can then activate said unit in a suitable manner or operate it in the provided manner in a provided process.

Furthermore, a parameter unit 18, also as a component of the drawer assembly, is assigned to each control function unit, parameter unit 18 allowing for the predefined or controllable parameterization of the respective control function unit (12 or 30 in the exemplary embodiment of FIG. 1), in particular in conjunction with an actualization or configuration unit 20: Preferably by a central control from central system unit 38, operating data provided for the operation or other parameter for configuring or operating the respective control function unit can be defined and can be changed in a suitable manner, for example if parameter changes are required because of a changed process sequence. Additionally or alternatively, in particular assembly 20 allows for the realization of permanent parameter changes, such as normal system updates, which can be additionally and advantageously filed in non-volatile storage means 22 which are also assigned to each drawer assembly (and typically also realized on the circuit board of the drawer).

Furthermore, the exemplary embodiment of FIG. 1 illustrates a protocol unit 44 (which is centralized and assigned to the common, stationary unit 38 in the present case) which collects operating data (including configuration data and changes thereof), which files said data in a suitable manner in storage means 46 and which can provide said data for the purpose of a preferably external evaluation, for example a quality assurance or similar control measures in the sensitive bioprocess area.

When the device, which is shown in a schematic manner in FIG. 1, is used, operating personnel (not specifically trained with respect to the technology or with respect to the hardware requirements) can select suitable control function units for a respective bio-(technical) process, when required, assemble said control function units in (normally generic and exchangeable) drawer assemblies (alternatively, said preassembled drawer assemblies and the corresponding control function units are already available), and the equipped drawer assemblies can then be inserted, in principle at any position, into the reception shafts of the frame means of the device housing. An electronic or electrical contact (more preferably realized in a spring-supported manner) is preferably also realized by means of the mechanical fixation (to be explained below), a device (shown in a schematic manner in FIG. 1) thus being configurable and modifiable for a wide range of bioprocess applications in a highly flexible and reliable manner while minimizing modification times, and said realization being particularly preferably suitable for a laboratory, development and research context (but not generally limited to said context), in particular with respect to the advantageous flexibility and savings in time during the modification.

On the basis of FIGS. 2 to 5, the exemplarily mechanical realization of the exemplary embodiment shown in a schematic manner in FIG. 1 is explained below, the control function units protruding on the face or front side and shown in the perspective view of the device housing in FIG. 2 being realized as pumps (30 in the generic diagram of FIG. 1) engaging in fluid communication into reactor vessel 26 in a provided manner via fluid lines 28.

Figure 2:
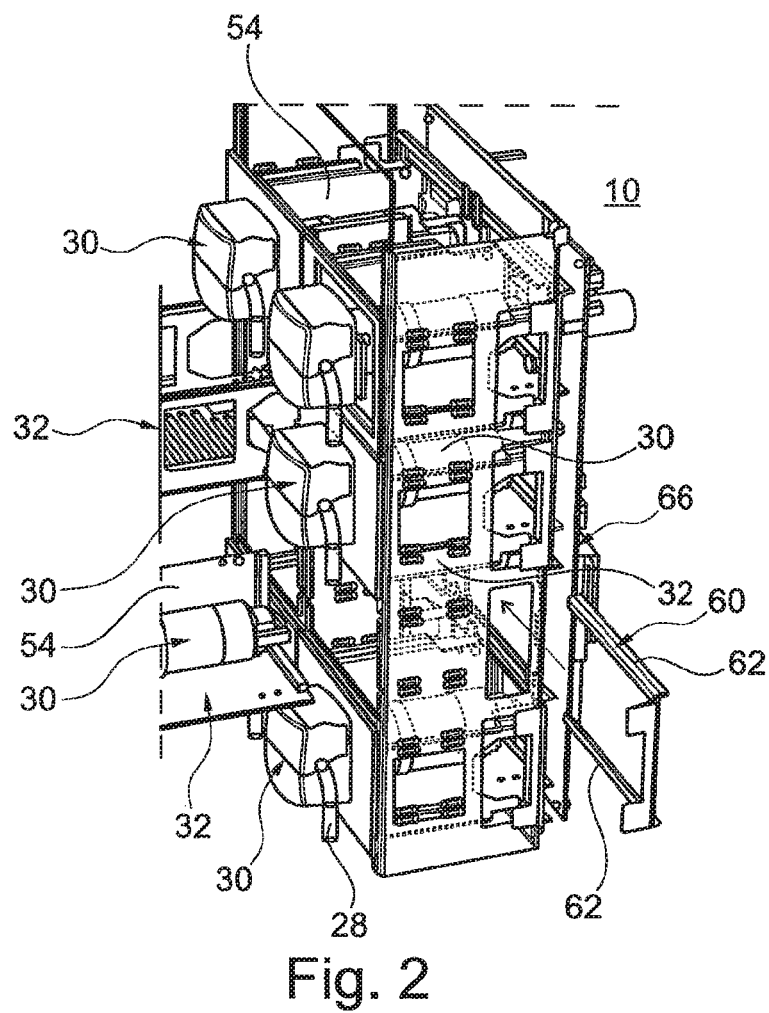
FIG. 2 is a perspective view of a mechanical and constructive realization of the bioprocess control device of an exemplary embodiment which has an open housing, an assembled plurality of control function units received in drawer assemblies and assemblies which are exemplarily shown in a detached manner

It illustrates that each of drawer assemblies 32 has a drawer frame structure 52 which contacts a plane front or face surface 50 and which allows for a longitudinal insertion movement into the shaft and frame structure illustrated in FIG. 2 in a manner known per se.

Figure 3:
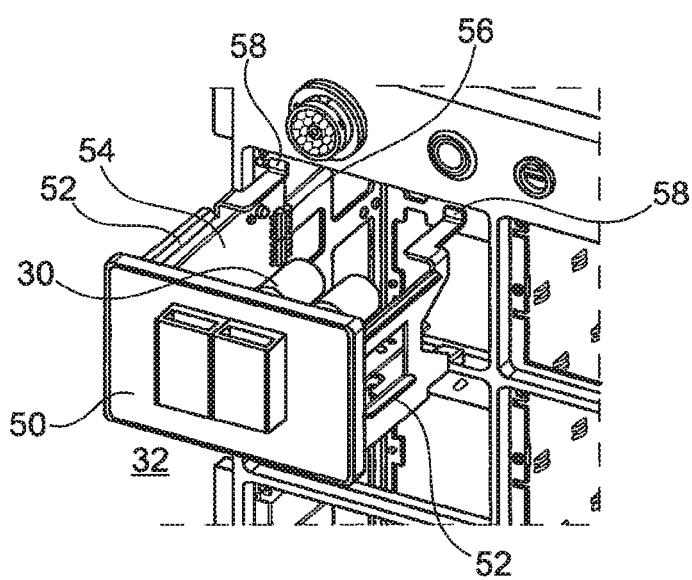
FIG. 3 to FIG. 5 are different detailed views of the device housing of the exemplary embodiment of FIG. 2, in particular of the (stationary) housing frame means in interaction with a drawer assembly and with the lock means which are exemplarily realized in a bracket-like manner.
Figure 4:
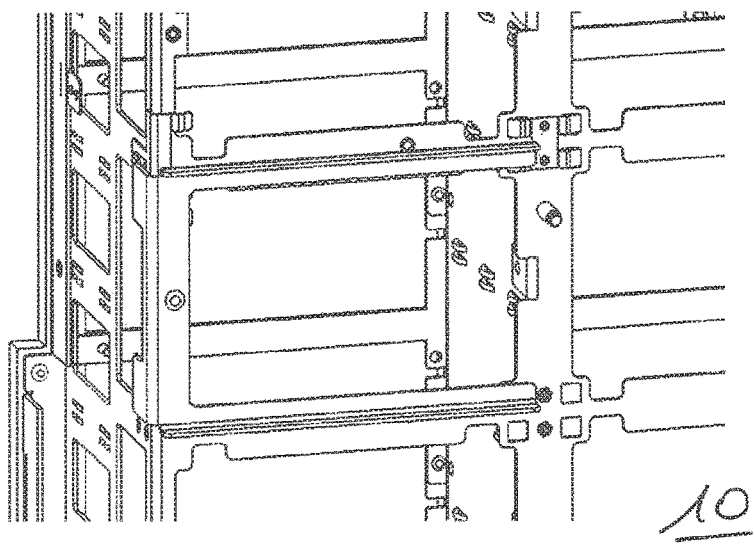
Figure 5:
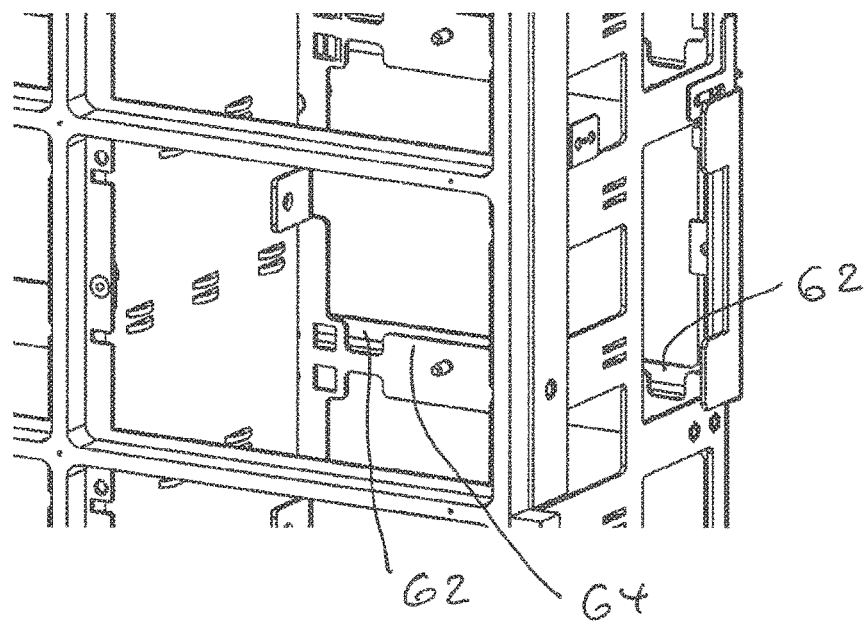

In particular the perspective view of FIG. 3 shows the vertical disposition on the left side (in the insertion direction) of a circuit board 54 which is assigned to drawer assembly 32; its plug unit 56 at the end shows an example of the realization of a (sprung) interface coupling to the electrical connection system 48 (FIG. 1).

Additionally, in particular FIG. 3 of drawer assembly 32 which is partially extracted shows an angle or vertical flange section 58 on the side of the housing which, in conjunction with a rectangular lock assembly (lock means) 60 in the form of a bracket, causes the locking according to the invention of a drawer assembly at or in the housing (or the housing frame means): Lock assembly 60 to be inserted in the manner shown in FIG. 2 at right angles to the insertion direction of the drawer assemblies and therefore from a housing or frame side of the device housing (when the housing panel is removed) engages into or onto a guiding 64 of the housing frame means by means of elongated rod sections 62 in such a manner that the pair of rod section engages in a locking manner with angled flange sections 58 when lock assembly 60 is inserted.

Furthermore, it can be seen that the respective front surfaces 50 of the plurality of drawer assemblies realize a continuous, plane and uninterrupted front surface of the device housing (FIG. 2)—with the exception of protruding sections of the respective control function units—in the inserted state, advantageous conditions for a cleaning, disinfection or similar treatments in the biological laboratory context thus being in particular met by means of said realization.

In FIGS. 2 to 5, the central supply, identification and protocol electronics assembly which is schematically shown in FIG. 1 as a group which is referenced with reference sign 38 is realized on a rear circuit board assembly 66 which is opposite to the respective front surfaces and which is covered by housing panels (which can be removed in a suitable manner) when it is used, the housing panels also covering the lateral, upper and lower surfaces.

The figures do not show the possibility of adding an additional frame or housing structure outside the housing to device housing 10 in order to receive possible additional control function units, in particular for the application in which the number of shafts (and therefore the possibilities of receiving control function units received in drawer assemblies) is not sufficient for an intended bioprocess and additional units of this sort must be removed. In an advantageous embodiment according to the invention, such additional frame means do not have to be provided with a separate central electronics assembly (38 or circuit board realization 66); instead, said electronics assembly can be realized by a suitable additional bus coupling, by analogy with connection structure 48 in FIG. 1.

The invention claimed is:

1. A bioprocess control device, comprising:
    a device housing (10) having a stationary housing frame, wherein the stationary housing frame includes a plurality of shaft receptions;
    a plurality of modular drawer assemblies (14, 32) moveable relative to the stationary housing frame between an opening and/or removal position and an operating or closure position;
    a plurality of control function units (12, 30) of different types, wherein each of the plurality of control function units is arranged within a modular drawer assembly of the plurality of modular drawer assemblies, and wherein the plurality of control function units are designed and provided for bioprocesses and configured or configurable for control, conveying, measuring and/or sensor functionalities;
    a lock means (60, 58);
    an electrical energy source (40) electrically coupled to the plurality of modular drawer assemblies; and
    system identification means (42) connected to the plurality of control function units;
    wherein each of the plurality of modular drawer assemblies is arranged in a shaft reception of the plurality of shaft receptions,
    wherein each of the shaft receptions comprises an interface plug unit that is coupled to a corresponding interface plug unit of a modular drawer assembly of the plurality of modular drawer assemblies, when the plurality of modular drawer assemblies are in the operating or closure position,
    wherein each of the plurality of modular drawer assemblies is configured to be received by any one of the plurality of shaft receptions,
    wherein, when, the modular drawer assemblies (14, 32) are in the opening and/or removal position each of the modular drawer assemblies is configured to receive a control function unit of the plurality of control function units,
    wherein each of the plurality of modular drawer assemblies further comprising a function identification unit (16) configured to identify a type of control function unit of the plurality of control function units of different types that is plugged in to a respective modular drawer assembly of the plurality of modular drawer assemblies, and wherein the function identification unit is configured to convey the type of control function unit to the system identification means (42),
    wherein, when, the plurality of modular drawer assemblies are in the operating or closure position, each plurality of modular drawer assemblies is locked by the lock means (60, 58) to the device housing, wherein, in the operating or closure position, the control function unit is powered by the electrical energy source (40) and the type of the control function unit is identified by the system identification means (42) via the function identification units (16), and
    wherein the different types of the plurality of control function units is selected from a group consisting of pumps, valves, fluid heaters and/or fluid coolers, gas sensors, liquid sensors, and combinations thereof.

2. The device according to claim 1, further comprising an electronic process protocol means (44) connected to the function identification units (16) and/or to the system identification means (42) in such a manner that said process protocol means can record, store (46) and, for the purpose of processing, provide operating data, and configuration data which correspond, to an operation and/or a configuration of the plurality of control function units.

3. The device according to claim 1, wherein front outer surfaces (50) of the plurality of modular drawer assemblies realize an, at least sectionwise, continuous, outer surface of the device housing (10) in the operating or locking position.

4. The device according to claim 3, wherein front outer surfaces (50) of the plurality of modular drawer assemblies which are adjacent to one another are aligned in a tile-like manner and/or connected by additional sealing means in such a manner in a common operating or locking position that a continuous outer surface of the housing can be treated with liquid detergents while preventing the liquid detergents from entering between adjacent outer surfaces of the plurality of modular drawer assemblies.

5. The device according to claim 1, wherein the lock means comprise a lock assembly (60) which engages on an abutment and/or locking section (58) of a drawer assembly (32) of the plurality of modular drawer assemblies in a mechanical manner, and which provides a connection between the drawer assembly and the housing frame which blocks a pushing out when the drawer assembly is inserted into the shaft receptions of the stationary housing frame.

6. The device according to claim 5, wherein the lock assembly is a rod- and/or bracket lock assembly that is inserted into the modular drawer assembly for the purpose of locking at an angle of more than 0°, in relation to a direction of the insertion of the drawer assembly and/or wherein said lock assembly is realized for common locking of a plurality of inserted drawer assemblies.

7. A bioprocess system comprising:
    at least one bioprocess reactor; and
    the bioprocess control device according to claim 1.

8. A method for configuring a bioprocess system, comprising the steps:
    providing bioprocess system according to claim 7;
    assembling the plurality of control function units in corresponding drawer assemblies;
    assembling the plurality of drawer assemblies in the device housing;
    operating the bioprocess control device in order to perform a first biological, pharmaceutical, chemical and/or biotechnical process in the at least one bioprocess reactor;
    replacing at least one of the plurality of drawer assemblies by an additional drawer assembly of the plurality of drawer assemblies provided with an additional control function unit; and operating the bioprocess control device in order to perform a second biological, pharmaceutical, chemical and/or biotechnical process.

9. The bioprocess control device according to claim 1, wherein the plurality of control function units are assignable to a bioprocess reactor.

10. The device according to claim 1, wherein the plurality of function identification units (16) is provided on an electrical circuit board (54) of the at least one modular drawer assembly.

11. The device according to claim 6, wherein the angle is more than 45°.

* * * * *